US00PP12880P2

(12) United States Plant Patent
Wicki-Freidl

(10) Patent No.: US PP12,880 P2
(45) Date of Patent: Aug. 27, 2002

(54) BIDENS PLANT NAMED 'PETERS GOLDTEPPICH'

(75) Inventor: Peter Wicki-Freidl, Nev St.-Johann (CH)

(73) Assignee: Innovaplant GmbH & Co. KG, Gensingen (DE)

( * ) Notice: Subject to any disclaimer, the term of this patent is extended or adjusted under 35 U.S.C. 154(b) by 0 days.

(21) Appl. No.: 09/545,905

(22) Filed: Apr. 9, 2000

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,261 P * 3/2000 Theobald ..... Plt./263

OTHER PUBLICATIONS

UPOV ROM GTITM Computer Database, GTI JOUVE retrieval software 2000/04, citations for 'Peters Goldteppich' Aug. 2000.*

* cited by examiner

*Primary Examiner*—Bruce R. Campell
*Assistant Examiner*—Wendy Couchoud Baker
(74) *Attorney, Agent, or Firm*—C. A. Whealy

(57) ABSTRACT

A distinct cultivar of Bidens plant named 'Peters Goldteppich', characterized by its low-growing and cascading plant habit; freely branching, dense and bushy appearance; high vigor; small dark green foliage; early and continuous flowering; and large golden yellow inflorescences held above and beyond the foliage on wiry peduncles.

1 Drawing Sheet

BACKGROUND OF THE INVENTION

The present Invention relates to a new and distinct cultivar of Bidens plant, botanically known as *Bidens ferulifolia* and referred to by the cultivar name Peter Goldteppich.

The new Bidens was discovered by the Inventor in Neu St. Johann, Switzerland, in the spring, 1996, within a population of seedling progeny from various random crosses of *Bidens ferulifolia* cultivar Goldmarie, not patented, and *Bidens ferulifolia* cultivar Procumbens, not patented, that were made in the winter, 1995. The selection of this plant was based on its earlier flowering, more compact and denser growth habit, and better overall plant performance compared to the parent cultivars.

Asexual propagation of the new cultivar by terminal cuttings at Neu St. Johann, Switzerland, has shown that the unique features of this new Bidens are stable and reproduced true to type in successive generations.

SUMMARY OF THE INVENTION

The following traits have been repeatedly observed and are determined to be the unique characteristics of 'Peters Goldteppich'. Therse characteristics in combination distinguish 'Peters Goldteppich' as a new and distinct cultivar:

1. Low-growing and cascading plant habit.
2. Freely branching, dense and bushy appearance.
3. High vigor.
4. Small dark green foliage.
5. Early and continuous flowering.
6. Large golden yellow inflorescences held above and beyond the foliage on wiry peduncles.

The new Bidens can be compared to plants of the Bidens cultivar Innbid, disclosed in U.S. Plant Pat. No. 11,261.

However, in side-by-side comparisons conducted in Gensingen, Germany, plants of the new Bidens have darker green leaves, larger inflorescences, and flower earlier than plants of the cultivar Innbid. In addition, plants of the new Bidens have a low-growing cascading plant habit whereas plants of the cultivar Innbid are mostly upright.

The cultivar Peters Goldteppich has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new Bidens, showing the colors as true as it is reasonably possible to obtain in colored reproductions of this type. Colors in the photographs may differ slightly from the color values cited in the detailed botanical description which more accurately describe the actual colors of the new Bidens.

The photograph at the top of the sheet comprises a top perspective view of a typical flowering plant of 'Peters Goldteppich'.

The photograph at the bottom of the sheet is a close-up view of upper and loser surfaces of typical leaves, typical inflorescence buds, and lower and upper surfaces of typical inflorescences of 'Peters Goldteppich'.

DETAILED BOTANICAL DESCRIPTION

The following observations, measurements and values describe 20-cm containers with three plants of the new cultivar grown in Bonsall, Calif., under outdoor, full-sun conditions with day temperatures ranging from 21 to 35° C.

and night temperatures ranging from 13 to 18° C. Plants used for the description were about six to eight weeks old.

Color references are made to The Royal Horticultural Society Colour Chart except where general terms of ordinary dictionary significance are used.

Botanical classification: *Bidens ferulifolia* cultivar Peters Goldteppich.

Parentage: Selection from seedling progeny from random crosses of *Bidens ferulifolia* cultivar Goldmarie (not patented) and *Bidens ferulifolia* cultivar Procumbens (not patented).

Propagation:

*Type*.—By terminal cuttings.

*Time to initiate roots, summer*.—About 14 days at 22° C.

*Time to initiate roots, winter*.—About 16 days at 20° C.

*Time to develop roots, summer*.—About 21 days at 22° C.

*Time to develop roots, winter*.—About 25 days at 20° C.

*Root description*.—Fibrous and freely branching.

Plant description:

*Appearance*.—Herbaceous container and garden plant. Low-growing and spreading, cascading growth habit. Full plants with dense foliage and inflorescences held above and beyond the foliage on wiry peduncles.

*Crop time*.—From planting rooted cuttings, about 6 to 8 weeks are required to produce a finished, flowering plant in a 10-cm container.

*Vigor*.—Vigorous.

*Plant height*.—About 15 cm.

*Plant spread*.—About 47 cm.

*Lateral branches*.—Quantity: Freely branching, about 8 lateral branches. Pinching, that is, removal of terminal apices, enhances branching. Length: About 30 cm. Diameter: About 2 mm. Internode length: About 4.75 cm. Texture: Pubescent. Color: 144B with some anthocyanin, 79D.

*Foliage description*.—Leaves opposite, single. Length: About 3.2 cm. Width: About 2 cm. Shape: Dissected; pinnatifid. Apex: Narrowly acute. Base: Attenuate. Texture: Smooth. Petiole length: About 1 cm. Petiole diameter: About 2 mm. Color: Young foliage, upper surface: 138A. Young foliage, lower surface: 138B. Fully expanded foliage, upper surface: 147A; venation, 147B. Fully expanded foliage, lower surface: 147B; venation, 147B. Petiole: 138B.

Inflorescence description:

*Appearance*.—Daisy-type composite inflorescence form; actinomorphic. Disc and ray florets arranged acropetally on a capitulum. Inflorescences displayed above and beyond the foliage on wiry peduncles; peduncles arising from upper leaf axils. Continuously flowering, numerous inflorescences open at the same time. Inflorescences last about one week on the plant; persistent. Floriferous with typically about 65 inflorescence buds and open inflorescences per plant.

*Flowering response*.—Plants flower continuously from March/April to October/November in the Northern Hemisphere.

*Fragrance*.—Not detected.

*Inflorescence bud*.—Length: About 1.2 mm. Diameter: About 7 mm. Shape: Ovoid. Color: 12A.

*Inflorescence size*.—Diameter: About 4 cm. Depth (height): About 1 cm. Diameter of disc: About 1 cm.

*Ray florets*.—Length: About 2.2 cm. Width: About 1.4 cm. Shape: Oblong to elliptic. Apex: Broadly acute or slightly tri-dentate. Base: Acute. Margin: Entire. Aspect: Mostly flat. Texture: Smooth, satiny. Number of ray florets per inflorescence: About five in a single whorl. Color: When opening, upper surface: 13A. When opening, lower surface: 13B. Fully opened, upper surface: 12A. Fully opened, upper surface: 12B.

*Disc florets*.—Shape: Tubular; fluted at apex. Number of disc florets per inflorescence: About 94. Length: About 7 mm. Diameter: About 1 mm. Color: Immature: 4B. Mature: 5A.

*Phyllaries*.—Quantity: About 15 in three whorls. Length: About 5 mm. Shape: Elongated elliptic. Apex: Rounded. Margin: Entire. Texture: Slightly pubescent. Color: Upper surface: 137A. Lower surface: 137B.

*Peduncle*.—Length: First peduncle: About 9.2 cm. Second peduncle: About 10.5 cm. Third peduncle: About 10.5 cm. Aspect: Flexible, wiry, moderately strong; inflorescences held above and beyond foliage; angled about 45° to the stem. Texture: Smooth, velvety. Color: 144B.

*Reproductive organs*.—Androecium: Present on disc florets only. Stamen quantity: Five per disc floret. Anther shape: Elongate. Anther size: About 2 mm. Anther color: 177A. Pollen amount: Scarce. Pollen color: 13A. Gynoecium: Present on ray and disc florets. Pistil length: About 6 mm. Stigma shape: Recurved, bipartite. Stigma color: 12A. Style length: About 3 mm. Style color: 12C. Ovary color: 4A. Seed: Seed development has not been observed.

Disease resistance: Resistance to pathogens common to Bidens has not been observed on plants of the new Bidens.

It is claimed:

1. A new and distinct cultivar of Bidens plant named 'Peters Goldteppich', as illustrated and described.

* * * * *

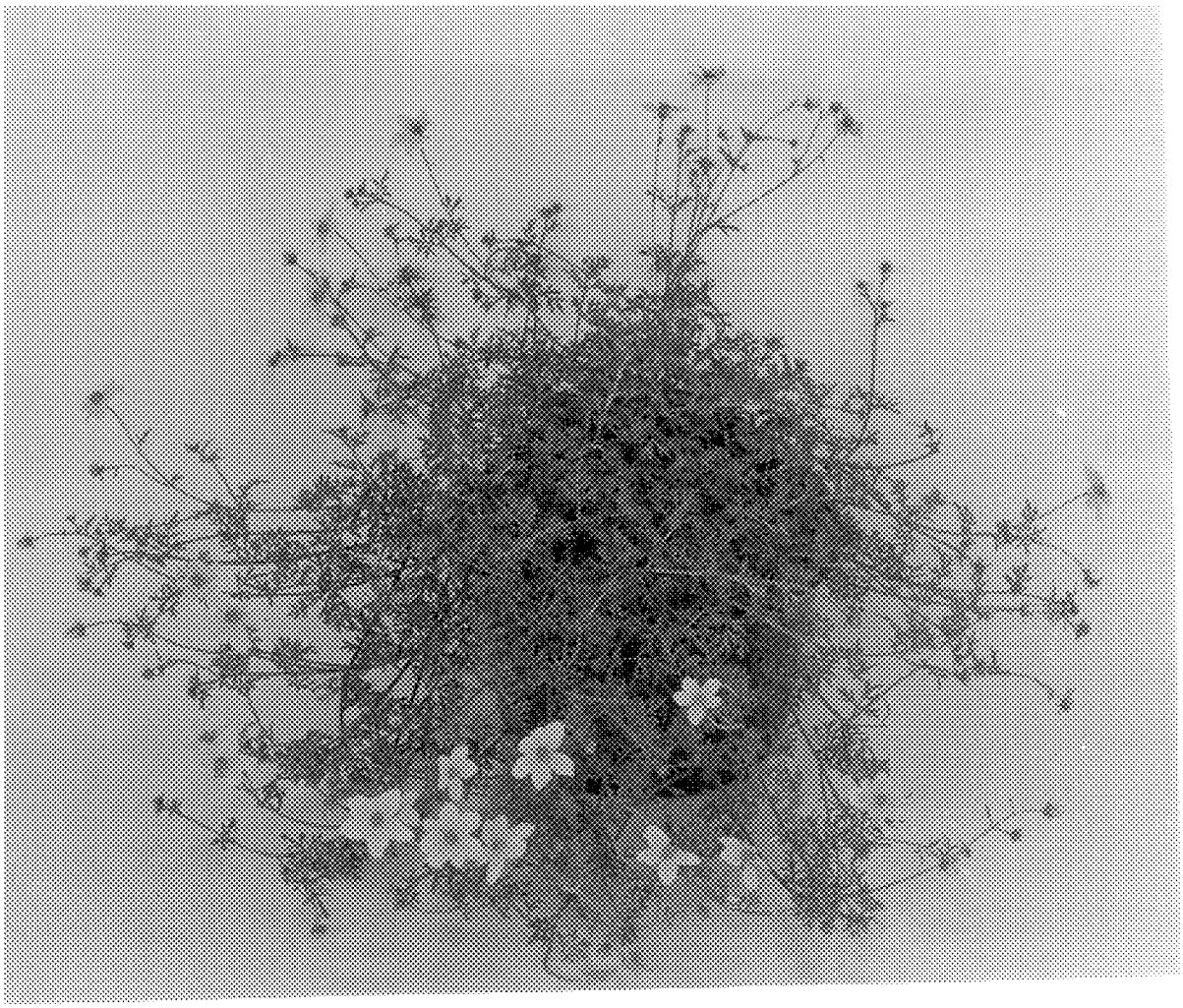
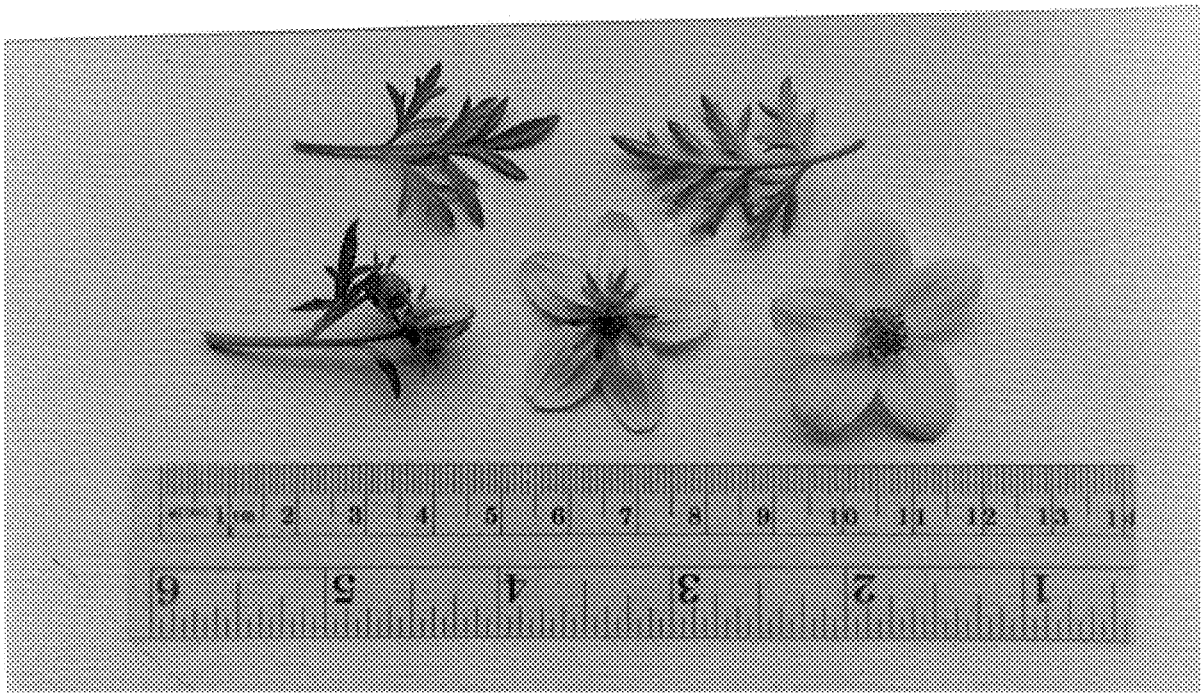
1 2 3 4 5 6 7 8 9 10 11 12 13 14
1 2 3 4 5 6